United States Patent [19]
Rosok et al.

[11] Patent Number: 4,834,976
[45] Date of Patent: May 30, 1989

[54] MONOCLONAL ANTIBODIES TO PSEUDOMONAS AERUGINOSA FLAGELLA

[75] Inventors: Mae J. Rosok, Seattle; Mark E. Lostrom, Redmond, both of Wash.

[73] Assignee: Genetic Systems Corporation, Seattle, Wash.

[21] Appl. No.: 946,554

[22] Filed: Dec. 24, 1986

Related U.S. Application Data

[63] Continuation-in-part of Ser. No. 881,984, Jul. 3, 1986.

[51] Int. Cl.$^4$ ..................... A61K 39/40; G01N 33/53
[52] U.S. Cl. .......................................... 424/87; 435/7; 435/240.27; 435/804; 435/875; 436/512; 436/513; 436/519; 436/548; 436/811; 530/387; 935/100; 935/107; 935/108
[58] Field of Search ................. 424/87; 435/7, 172.3, 435/804, 810, 875, 240.27; 436/501, 512, 513, 536, 519, 548, 811; 530/387; 935/100, 107, 108

[56] References Cited

U.S. PATENT DOCUMENTS

| | | | |
|---|---|---|---|
| 4,157,389 | 6/1979 | Homma et al. | 424/87 X |
| 4,443,549 | 4/1984 | Sadowski | 424/85 X |
| 4,563,418 | 1/1986 | Ward, Jr. | 435/29 X |
| 4,596,769 | 6/1986 | Shockman et al. | 435/68 X |
| 4,624,921 | 11/1986 | Larrick et al. | 935/100·X |
| 4,677,070 | 6/1987 | Larrick et al. | 424/87 X |
| 4,772,464 | 9/1988 | Rutherford et al. | 424/87 |
| 4,777,136 | 10/1988 | Young | 436/548 X |

OTHER PUBLICATIONS

Ansorg, R., 1978, Flagella Specific H Antigenic Schema of *Pseudomonas aeruginosa, Zbl. Bakt. Hyg.,* I. Abt. Orig. A 242:228-238 (Abstract only).
Ansorg, R. et al., 1984, Differentiation of the Major Flagellar Antigens of *Pseudomonas aeruginosa* by the Slide Coagulation Technique, *J. Clin. Microbiol.* 20:84-88.
Craven, R. C., et al., 1981, Motility and Chemotaxis of Three Strains of *Pseudomonas aeruginosa* used for Virulence Studies, *Can. J. Microbiol.* 27:458-460.
Holder, I. A., et al., 1982, Flagellar Preparations from *Pseudomonas aeruginosa:* Animal Protection Studies, *Infect. Immun.* 35:276-280.
Holder, I. A., et al., 1986, Experimental Studies of the Pathogenesis of Infections due to *Pseudomonas aeruginosa:* Immunization Using Divalent Flagella Preparations, *J. Trauma* 26:118-122.
Lanyi, B., 1970, Serological Properties of *Pseudomonas aeruginosa, Acta Microbiol. Acad. Sci.* Hung. 17:35-48.
Luzar, M. A. et al., 1985, Avirulence and Altered Physiological Properties of Cystic Fibrosis Strains of *Pseudomonas aeruginosa, Infect. Immun.* 50:572-576.
Luzar, M. A. et al., 1985, Flagella and Motility Alterations in *Pseudomonas aeruginosa* Strains from Patients with Cystic Fibrosis: Relationship to a Patient Clinical Condition, *Infect. Immun.* 50:577-582.
McManus, A. T. et al., 1979, Bacterial Motility: A Component in Experimental *Pseudomonas aeruginosa* Burn Wound Sepsis, *Burns* 6:235-239.
Montie, T. C. et al., 1982, Loss of Virulence Associated with Absence of Flagellum in an Isogenic Mutant of *Pseudomonas aeruginosa* in the Burned-Mouse Model, *Infect. Immun.* 38:1296-1298.

*Primary Examiner*—Robert J. Warden
*Assistant Examiner*—Richard Wagner
*Attorney, Agent, or Firm*—Townsend and Townsend

[57] ABSTRACT

Cell lines have been produced that secrete monoclonal antibodies capable of binding to the flagellar proteins of selected *Pseudomonas aeruginosa* strains. Some of these antibodies have been found to be protective against lethal challenges of *P. aeruginosa.* Pharmaceutical compositions containing these antibodies, which can be in combination with other monoclonal antibodies, blood plasma fractions and antimicrobial agents, and the prophylactic and therapeutic use of such compositions in the management of infections, are included.

Prior to filing this application, the continuous transformed cell lines PaF4 IVE8, FA6 IIG5, 20H11, and 21B8, described herein, were deposited in the America Type Culture Collection and given the designations HB9129, HB9130, CRL 9300, and CRL 9301, respectively.

22 Claims, No Drawings

MONOCLONAL ANTIBODIES TO PSEUDOMONAS AERUGINOSA FLAGELLA

This application is a continuation-in-part of application Ser. No. 881,984 filed July 3, 1986.

FIELD OF THE INVENTION

The present invention relates to the application of immunological techniques to provide novel materials useful in diagnosing and treating bacterial infections and, more particularly, to the production and application of monoclonal antibodies that are capable of recognizing *Pseudomonas aeruginosa* flagella.

BACKGROUND OF THE INVENTION

Gram-negative disease and its most serious complications, e.g., bacteremia and endotoxemia, are the cause of significant morbidity and mortality in human patients. This is particularly true of the gram-negative organism *Pseudomonas aeruginosa*, which has been increasingly associated with bacterial infections, especially nosocomial infections, over the last fifty years.

During the past few decades, antibiotics have been the therapy of choice for controlling gram-negative disease. The continued high morbidity and high mortality associated with gram-negative bacterial disease, however, is indicative of the limitations of antibiotic therapy, particularly with respect to *P. aeruginosa*. (See, for example, Andriole, V. G., "*Pseudomonas Bacteremia:* Can Antibiotic Therapy Improve Survival?", *J. Lab. Clin. Med.* [1978] 94:196–199). This has prompted the search for alternative methods of prevention and treatment.

One method that has been considered is augmentation of the host's immune system by active or passive immunization. For instance, it has been observed that active immunization of humans or experimental animals with whole cell bacterial vaccines or purified bacterial endotoxins from *P. aeruginosa* leads to the development of specific opsonic antibodies directed primarily against determinants on the repeating oligosaccharide units of the lipopolysaccharide (LPS) molecules located on the outer cell membrane of *P. aeruginosa* (see Pollack, M., *Immunoglobulins: Characteristics and Uses of Intravenous Preparations,* Alving, B. M., and Finlayson, J. S., eds., pp. 73–79, U.S. Department of Health and Human Services, 1979). Such antibodies, whether actively engendered or passively transferred, have been shown to be protective against the lethal effects of *P. aeruginosa* infection in a variety of animal models (Pollack, supra) and in some preliminary investigations with humans (see Young, L. S. and Pollack, M., *Pseudomonas aeruginosa*, Sabath, L., ed., pp. 119–132, Hans Huber, 1980).

The above reports suggest that immunotherapeutic approaches could be utilized to prevent and treat bacterial disease due to *P. aeruginosa*, such as by administering pooled human immune globulins that contain antibodies against the infecting strain(s). Human immune globulins are defined herein as that portion of fractionated human plasma that is enriched for antibodies, among which are represented specific antibodies to strains of *P. aeruginosa*. Due to certain inherent limitations in using human immune globulin components, this approach to treatment of disease due to *P. aeruginosa* remains under investigation (see, for example, Collins, M. S. and Roby, R. E., *Am. J. Med.*, 76(3A):168–174, [1984]), and as yet there are no commercial products available utilizing these components.

One such limitation associated with immune globulin compositions is that they consist of pools of samples from a thousand or more donors, such samples having been preselected for the presence of particular anti-Pseudomonas antibodies. This pooling leads to an averaging of individual antibody titers which, at best, results in modest increases in the resultant titer of the desired antibodies.

Another limitation is that the preselection process itself requires expensive, continuous screening of the donor pool to assure product consistency. Despite these efforts, the immune globulin products can still have considerable variability from batch to batch and among products from different geographic regions.

Yet another such limitation inherent in immune globulin compositions is that their use results in the coincident administration of large quantities of extraneous proteinaceous substances (which may include viruses, such as those recently shown to be associated with Acquired Immune Deficiency Syndrome, or AIDS), having the potential to cause adverse biologic effects. The combination of low titers of desired antibodies and high content of extraneous substances may often limit, to suboptimal levels, the amount of specific and thus beneficial immune globulin(s) administrable to the patient.

In 1975 Kohler and Milstein reported their seminal discovery that certain mouse cell lines could be fused with mouse spleen cells to create hybridomas each of which which would secrete antibodies of a single specificity, i.e., monoclonal antibodies (Kohler, G., and Milstein, C., *Nature,* 256:495–497 [1975]). With the advent of this technology it became possible, in some cases, to produce large quantities of exquisitely specific murine antibodies to a particular determinant or determinants on antigens. Subsequently, using later-developed technologies, it became possible to produce human monoclonal antibodies (see, e.g., U.S. Pat. No. 4,464,465, which is incorporated herein by reference).

It is recognized that in some situations mouse monoclonal antibodies or compositions of such antibodies may present problems for use in humans. For example, it has been reported that mouse monoclonal antibodies used in trial studies for the treatment of certain human disease can elicit an immune response that renders them noneffective (Levy, R. L., and Miller, R. A., *Ann. Rev. Med.*, 34:107–116 [1983]). However, with recent advances in recombinant DNA technology, such as the production of chimeric mouse/human monoclonal antibodies, these problems may be abated. Also, methods for the production of human monoclonal antibodies are now available (see, *Human Hybridomas and Monoclonal Antibodies,* Engleman, E. G., et al., eds., Plenum Publishing Corp. [1985], which is incorporated herein by reference).

Using hybridoma and/or cell transformation technology, a number of groups have reported the production of monoclonal antibodies protective against *P. aeruginosa* infections. Monoclonal antibodies have been produced that are reactive with various epitopes of *P. aeruginosa*, including single and multi-serotype specific surface epitopes, such as those found in LPS molecules of the bacteria (see, for example, commonly assigned pending U.S. patent application Ser. Nos. 734,624 and 807,394, which are both incorporated herein by reference). Also, protective monoclonal antibodies specific for *P. aeruginosa* exotoxin A have been produced (see, for example, commonly assigned U.S. patent application Ser. No. 742,170, which is incorporated herein by reference).

While utilizing monoclonal antibodies specific for the LPS region of *P. aeruginosa*, or the bacteria's exotoxins, may provide sufficient protection in some situations, generally it is preferable to have broader protection capability. For example, in prophylactic treatments for potential infections in humans, it would be preferable to administer an antibody or antibodies protective against a plurality of *P. aeruginosa* strains. Similarly, in therapeutic applications where the serotype(s) of the infecting strain(s) is not know, it would be preferable to administer an antibody or combination of antibodies effective against most, if not all, of the clinically important *P. aeruginosa* serotypes, ideally by providing antibodies reactive across traditional serotyping schemes.

One aspect of *P. aeruginosa* physiology that has been shown to contribute to the organism's virulence is motility, a capability resulting primarily from the presence of a flagellum (see, Montie, T., et al. [1982], *Infect. and Immun.*, 38:1296–1298). *P. aeruginosa* is characterized by having a single flagellum at one end of its rod-shaped structure. Burned mouse model studies have shown that a greater percentage of mice survived when non-motile *P. aeruginosa* strains were inoculated into experimental burns than if motile strains were utilized. (McManus, A., et al. [1980], *Burns*, 6:235–239 and Montie, T., et al. [1982], *Infect. and Immun.*, 38:1296–1298). Other studies on the pathogenesis of *P. aeruginosa* have alleged that animals immunized with flagella antigen preparations were protected when burned and infected with motile strains of the bacteria (see, Holder, I., et al. [1982], *Infect. and Immun.*, 35:276–280).

Importantly, *P. aeruginosa* flagella have been studied by serological methods and have been reported to fall into two major antigenic groups designated H1 and H2 by B. Lanyi (1970, *Acta Microbiol. Acad. Sci. Hung.*, 17:35–48) and type a and type b by Ansorg, R. (1978, *Zbl. Bakt. Hyg., I. Abt. Orig. A*, 242:228–238). Serological typing of flagella by both laboratories showed that H1 flagella (Lanyi, B., supra) or flagella type b (Ansorg, R., supra) was serologically uniform, i.e., no subgroups have been identified. This serologically uniform flagellar type will be referred to as type b. The other major antigen, H2 (Lanyi, B., supra) or type a flagella (Ansorg, R., supra) contained five subgroups. This antigen will be referred to as flagella type a, and the five subgroups as $a_0$, $a_1$, $a_2$, $a_3$, and $a_4$. The five subgroups of type a are expressed in varying combinations on different strains of type a bearing *P. aeruginosa* with the exception of the antigen $a_0$. The $a_0$ antigen was found on all type a flagella, although the degree to which it was expressed varied among strains.

A serotyping scheme based on the heat stable major somatic antigens of *P. aeruginosa* is referred to as the Habs scheme, which has recently been incorporated into the International Antigenic Typing System scheme. (See, Liu, *Int. J. Syst. Bacteriol.*, 33:256 [1983].) The flagella types of *P. aeruginosa* Habs reference strains have been characterized by immunofluorescence with polyclonal sera by R. Ansorg (1978, *Zbl. Bakt. Hyg., I. Abt. Orig. A*, 242:228–238) or by slide coagglutination (Ansorg, R., et al., 1984, *J. Clin. Microbiol.*, 20:84–88). Habs strains 2, 3, 4, 5, 7, 10, 11, and 12 are flagella type b bearing strains, and Habs strains 1, 6, 8, and 9 bear type a flagella. Thus, a large number of strains of *P. aeruginosa* could possibly be recognized by a small number of monoclonal antibodies specific for flagellar proteins.

Accordingly, there exists a significant need for monoclonal antibodies capable of reacting with epitopes on flagellar proteins and, in some cases, also providing protection against multiple serotypes of *P. aeruginosa*. Further, some of these antibodies should be suitable for use as prophylactic and therapeutic treatments of *P. aeruginosa* infections, as well as the diagnosis of such infections. The present invention fulfills these needs.

SUMMARY OF THE INVENTION

Novel cell lines are provided which can produce monoclonal antibodies capable of binding to flagella present on most strains of *P. aeruginosa* bacteria. The monoclonal antibodies specifically react with epitopes on flagella proteins of *P. aeruginosa* and can distinguish between type a and type b flagella of the bacteria. Additionally, a method is provided for treating a human susceptible to infection or already infected with *P. aeruginosa* by administering a prophylactic or therapeutic amount of a composition comprising at least one monoclonal antibody or binding fragment thereof capable of reacting with the flagella of *P. aeruginosa* strains, the composition preferably also including a physiologically acceptable carrier. The composition may also contain any one or more of the following: additional monoclonal antibodies capable of reacting with *P. aeruginosa* exotoxin A; monoclonal antibodies capable of reacting with serotype determinants on the LPS of *P. aeruginosa*; a gamma globulin fraction from human blood plasma; a gamma globulin fraction from human blood plasma, where the plasma may be obtained from a human exhibiting elevated levels of immunoglobulins reactive with *P. aeruginosa*; and one or more antimicrobial agents. Further, clinical uses of the monoclonal antibodies are provided, including the production of diagnostic kits.

DESCRIPTION OF THE SPECIFIC EMBODIMENTS

In accordance with the present invention, novel cells capable of producing monoclonal antibodies and compositions comprising such antibodies are provided, such compositions being capable of selectively recognizing the flagella present on a plurality of *P. aeruginosa* strains, where individual antibodies typically recognize one type of *P. aeruginosa* flagella. The subject cells have identifiable chromosomes in which the germ-line DNA from them or a precursor cell has rearranged to encode an antibody having a binding site for an epitope on a flagellar protein common among certain *P. aeruginosa* strains. For type a flagellar proteins, pan-reactive monoclonal antibodies can be produced; and for type b flagellar proteins, antibodies that are pan-reactive or react with at least about 70% of the flagellar bearing strains are included. These monoclonal antibodies can be used in a wide variety of ways, including diagnosis and therapy.

The monoclonal antibodies so provided are particularly useful in the treatment or prophylaxis of serious disease caused by *P. aeruginosa*. The surface proteins on the flagella of *P. aeruginosa* would be available for direct contact by the antibody molecules, thus likely inhibiting the motility of the organism and/or facilitating other effects beneficial to the infected hosts.

The preparation of monoclonal antibodies can be accomplished by immortalizing a cell line capable of expressing nucleic acid sequences that code for antibodies specific for an epitope on the flagellar proteins of multiple strains of P. aeruginosa. The immortalized cell line may be a mammalian cell line that has been transformed through oncogenesis, by transfection, mutation, or the like. Such cells include myeloma lines, lymphoma lines, or other cell lines capable of supporting the expression and secretion of the immunoglobulin, or binding fragment thereof, in vitro. The immunoglobulin or fragment may be a naturally-occurring immunoglobulin of a mammal other than the preferred mouse or human sources, produced by transformation of a lymphocyte, particularly a splenocyte, by means of a virus or by fusion of the lymphocyte with a neoplastic cell, e.g., a myeloma, to produce a hybrid cell line. Typically, the splenocyte will be obtained from an animal immunized against flagellar antigens or fragments thereof containing an epitopic site. Immunization protocols are well known and can vary considerably yet remain effective. (See, Golding, *Monoclonal Antibodies: Principles and Practice*, Academic Press, N.Y. [1983], which is incorporated herein by reference.)

The hybrid cell lines may be cloned and screened in accordance with conventional techniques, and antibodies in the cell supernatants detected that are capable of binding to P. aeruginosa flagellar determinants. The appropriate hybrid cell lines may then be grown in large-scale culture or injected into the peritoneal cavity of an appropriate host for production of ascites fluid.

In one embodiment of the present invention, the cells are transformed human lymphocytes that produce human monoclonal antibodies, preferably protective in vivo, to accessible epitopes specific for at least one flagellar protein. The lymphocytes can be obtained from human donors who are or have been exposed to the appropriate flagella-bearing strains of P. aeruginosa. A preferred cell-driven transformation process is described in detail in U.S. Pat. No. 4,464,465, which is incorporated herein by reference.

By virtue of having the antibodies of the present invention, which are known to be specific for the flagellar proteins, in some cases the supernatants of subsequent experiments may be screened in a competition assay with the subject monoclonal antibodies as a means to identify additional examples of anti-flagellar monoclonal antibodies. Thus, hybrid cell lines can be readily produced from a variety of sources based on the availability of present antibodies specific for the particular flagellar antigens.

Alternatively, where hybrid cell lines are available that produce antibodies specific for the subject epitopic sites, these hybrid cell lines may be fused with other neoplastic B-cells, where such other B-cells may serve as recipients for genomic DNA coding for the receptors. While rodent, particularly murine, neoplastic B-cells are most commonly utilized, other mammalian species may be employed, such as lagomorpha, bovine, ovine, equine, porcine, avian or the like.

The monoclonal antibodies may be of any of the classes or subclasses of immunoglobulins, such as IgM, IgD, IgA, IgE, or subclasses of IgG known for each species of animal. Generally, the monoclonal antibodies may be used intact, or as binding fragments, such as Fv, Fab, F(ab')$_2$, but usually intact.

The cell lines of the present invention may find use other than for the direct production of the monoclonal antibodies. The cell lines may be fused with other cells (such as suitably drug-marked human myeloma, mouse myeloma, or human lymphoblastoid cells), to produce hybridomas, and thus provide for the transfer of the genes encoding the monoclonal antibodies. Alternatively, the cell lines may be used as a source of the chromosomes encoding the immunoglobulins, which may be isolated and transferred to cells by techniques other than fusion. In addition, the genes encoding the monoclonal antibodies may be isolated and used in accordance with recombinant DNA techniques for the production of the specific immunoglobulin in a variety of hosts. Particularly, by preparing cDNA libraries from messenger RNA, a single cDNA clone, coding for the immunoglobulin and free of introns, may be isolated and placed into suitable prokaryotic or eukaryotic expression vectors and subsequently transformed into a host for ultimate bulk production. (See, generally, U.S. Pat. Nos. 4,172,124; 4,350,683; 4,363,799; 4,381,292; and 4,423,147. See also, Kennett et al., *Monoclonal Antibodies*, Plenum, New York [1980], and references cited therein, all of which are incorporated herein by reference.)

More specifically, in accordance with hybrid DNA technology, the immunoglobulins or fragments of the present invention may be produced in bacteria or yeast. (See, Boss, et al., *Nucl. Acid. Res.*, 12:3791 and Wood et al., *Nature* 314:446, both of which are incorporated herein by reference.) For example, the messenger RNA transcribed from the genes coding for the light and heavy chains of the monoclonal antibodies produced by a cell line of the present invention may be isolated by differential cDNA hybridization employing cDNA from BALB/c lymphocytes other than the subject clone. The mRNA that does not hybridize will be rich for the messages coding for the desired immunoglobulin chains. As necessary, this process can be repeated to further enhance the the desired mRNA levels. The subtracted mRNA composition may then be reverse-transcribed to provide for a cDNA mixture enriched for the desired sequences. The RNA may be hydrolyzed with an appropriate RNase and the ssDNA made double-stranded with DNA polymerase I and random primers, e.g., randomly fragmented calf thymus DNA. The resulting dsDNA may then be cloned by insertion into an appropriate vector, e.g., virus vectors, such as lambda vectors or plasmid vectors (such as pBR322, pACYC184, etc.). By developing probes based on known sequences for the constant regions of the light and heavy chains, those cDNA clones having the gene coding for the desired light and heavy chains can be identified by hybridization. Thereafter, the genes may be excised from the plasmids, manipulated to remove superfluous DNA upstream from the initiation codon or constant region DNA, and then introduced in an appropriate vector for transformation of a host and ultimate expression of the gene.

Conveniently, mammalian hosts (e.g., mouse cells) may be employed to process the chain (e.g., join the heavy and light chains) to produce an intact immunoglobulin, and furthermore, secrete the immunoglobulin free of the leader sequence, if desired. Alternatively, one may use unicellular microorganisms for producing the two chains, where further manipulation may be required to remove the DNA sequences coding for the secretory leader and processing signals, while providing for an initiation codon at the 5' terminus of the sequence coding for the heavy chain. In this manner, the immunoglobulins can be prepared and processed so as to be assembled and glycosylated in cells other than mammalian cells. If desired, each of the chains may be truncated so as to retain at least the variable region, which regions may then be manipulated to provide for other immunoglobulins or fragments specific for the flagellate epitopes.

The monoclonal antibodies of the present invention are particularly useful because of their specificity for antigens across almost all *P. aeruginosa* variants presently known. Also, some of the monoclonal antibodies are protective in vivo, permitting incorporation into pharmaceutical products, such as antibody combinations for bacterial infections.

Monoclonal antibodies of the present invention can also find a wide variety of utilities in vitro. By way of example, the monoclonal antibodies can be utilized for microorganism typing, for isolating specific *P. aeruginosa* strains, for selectively removing *P. aeruginosa* cells in a heterogeneous mixture of cells, or the like.

For diagnostic purposes, the monoclonal antibodies may either be labeled or unlabeled. Typically, diagnostic assays entail detecting the formation of a complex through the binding of the monoclonal antibody to the flagellum of the *P. aeruginosa* organism. When unlabeled, the antibodies find use in agglutination assays. In addition, unlabeled antibodies can be used in combination with other labeled antibodies (second antibodies) that are reactive with the monoclonal antibody, such as antibodies specific for immunoglobulin. Alternatively, the monoclonal antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available, and by way of example, some include those described in U.S. Pat. Nos. 3,817,827; 3,850,752; 3,901,654; 3,935,074; 3,984,533; 3,996,345; 4,034,074; and 4,098,876, all of which are incorporated herein by reference.

Commonly, the monoclonal antibodies of the present invention are utilized in enzyme immunoassays, where the subject antibodies, or second antibodies from a different species, are conjugated to an enzyme. When a sample containing *P. aeruginosa* of a certain serotype, such as human blood or lysate thereof, is combined with the subject antibodies, binding occurs between the antibodies and those molecules exhibiting the desired epitope. Such cells may then be separated from the unbound reagents, and a second antibody (labeled with an enzyme) added. Thereafter, the presence of the antibody-enzyme conjugate specifically bound to the cells is determined. Other conventional techniques well known to those skilled in the art may also be utilized.

Kits can also be supplied for use with the subject antibodies for detecting *P. aeruginosa* in solutions or the presence of *P. aeruginosa* flagellar antigens. Thus, the subject monoclonal antibody composition of the present invention may be provided, usually in a lyophilized form, either alone or in conjunction with additional antibodies specific for other gram-negative bacteria. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

The monoclonal antibodies, particularly human monoclonal antibodies, of this invention can also be incorporated as components of pharmaceutical compositions containing a therapeutic or prophylactic amount of at least one of the monoclonal antibodies of this invention with a pharmaceutically effective carrier. A pharmaceutical carrier should be any compatible, non-toxic substance suitable to deliver the monoclonal antibodies to the patient. Sterile water, alcohol, fats, waxes, and inert solids may be used as the carrier. Pharmaceutically accepted adjuvants (buffering agents, dispersing agents) may also be incorporated into the pharmaceutical composition. Such compositions can contain a single monoclonal antibody so as to be specific for strains of one flagellar type of *P. aeruginosa*. Alternatively, a pharmaceutical composition can contain two or more monoclonal antibodies to form a "cocktail." For example, a cocktail containing monoclonal antibodies against both types of flagella or against groups of the various *P. aeruginosa* strains (e.g., different serotypes) would be a universal product with activity against the great majority of the clinical isolates of that particular bacterium.

The mole ratio of the various monoclonal antibody components will usually not differ by more than a factor of 10, more usually by not more than a factor of 5, and will usually be in a mole ratio of about 1:1–2 to each of the other antibody components.

The monoclonal antibodies of the present invention may also be used in combination with existing blood plasma products, such as commercially available gamma globulin and immune globulin products used in prophylactic or therapeutic treatment of *P. aeruginosa* disease in humans. Preferably, for immune globulins the plasma will be obtained from human donors exhibiting elevated levels of immunoglobulins reactive with *P. aeruginosa*. (See generally, the compendium "Intravenous Immune Globulin and the Compromised Host," *Amer. J. Med.*, 76(3a), Mar. 30, 1984, pp. 1–231, which is incorporated herein by reference.)

The subject monoclonal antibodies can be used as separately administered compositions given in conjunction with antibiotics or antimicrobial agents. Typically, the antimicrobial agents may include an anti-pseudomonal penicillin (e.g., carbenicillin) in conjunction with an aminoglycoside (e.g., gentamicin, tobramycin, etc.), but numerous additional agents (e.g., cephalosporins) well-known to those skilled in the art may also be utilized.

The monoclonal antibodies and pharmaceutical compositions thereof of this invention are particularly useful for oral or parenteral administration. Preferably, the pharmaceutical compositions may be administered parenterally, i.e., subcutaneously, intramuscularly or intravenously. Thus, this invention provides compositions for parenteral administration which comprise a solution of the monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, i.e., from less than about 0.5%, usually at or at least about 1% to as much as 15 or 20% by weight and will be selected primarily based on fluid volumes, viscosities, etc., preferably for the particular mode of administration selected.

Thus, a typical pharmaceutical composition for intramuscular injection could be made up to contain 1 ml sterile buffered water, and 50 mg of monoclonal antibody. A typical composition for intravenous infusion could be made up to contain 250 ml of sterile Ringer's solution, and 150 mg of monoclonal antibody. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference.

The monoclonal antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present monoclonal antibodies or a cocktail thereof can be administered for the prophylactic and/or therapeutic treatment of *P. aeruginosa* infections. In therapeutic application, compositions are administered to a patient already infected with one or more *P. aeruginosa* serotypes, in an amount sufficient to cure or at least partially arrest the infection and its complications. An amount adequate to accomplish this is defined as a "therapeutically effective dose." Amounts effective for this use will depend upon the severity of the infection and the general state of the patient's own immune system, but generally range from about 1 to about 200 mg of antibody per kilogram of body weight with dosages of from 5 to 25 mg per kilogram being more commonly used. It must be kept in mind that the materials of this invention may generally be employed in serious disease states, that is, life-threatening or potentially life-threatening situations, especially bacteremia and endotoxemia, due to *P. aeruginosa*.

In prophylactic applications, compositions containing the present antibody or a cocktail thereof are administered to a patient not already infected by *P. aeruginosa* to enhance the patient's resistance to such potential infection. Such an amount is defined to be a "prophylactically effective dose." In this use, the precise amounts again depend upon the patient's state of health and general level of immunity, but generally range from 0.1 to 25 mg per kilogram, especially 0.5 to 2.5 mg per kilogram.

Single or multiple administrations of the compositions can be carried out with dose levels and pattern being selected by the treating physician. In any event, the pharmaceutical formulations should provide a quantity of the antibody(ies) of this invention sufficient to effectively treat or prophylax the patient.

EXPERIMENTAL

EXAMPLE 1

Example 1 demonstrates the methodology used to prepare a murine monoclonal antibody that binds specifically to *P. aeruginosa* flagella.

Three-month-old BALB/c mice were immunized intraperitoneally eight times with viable *P. aeruginosa* Fisher immunotype 1 and Fisher immunotype 2 (A.T.C.C. #27312 and #27313) bacteria every one to two weeks for a total of nine weeks. The initial doses of bacteria were $8 \times 10^6$ and $1 \times 10^7$ organisms per mouse for *P. aeruginosa* Fisher immunotype 1 and Fisher immunotype 2, respectively, and the dosage was increased 30- to 60-fold during the course of immunizations.

Three days after the last injection, the spleen from one mouse was removed aseptically and a single cell suspension was prepared by gentle rotation of the organ between the frosted ends of two sterile glass slides. Spleen mononuclear cells were combined in a 4:1 ratio with log phase mouse myeloma cells (NSI-1, obtained from Dr. C. Milstein, Molecular Research Council, Cambridge, England) and fused to create hybridomas according to the procedure described by Tam et al. (1982, *Infect. Immun.*, 36:1042–1053). The final hybrid cell suspension was diluted to a concentration of $1.5 \times 10^6$ cells per ml in RPMI-hybrid-HAT (RPMI 1640 [Gibco, Grand Island, N.Y.] containing 15% heat-inactivated fetal calf serum, 1 mM sodium pyruvate, 100 µg/ml of penicillin and streptomycin, $1.0 \times 10^{-4}$ M hypoxanthine, $4.0 \times 10^{-7}$ M aminopterin, and $1.6 \times 10^{-5}$ M thymidine), which included $2.0 \times 10^6$ per ml freshly prepared BALB/c thymocytes as feeder cells.

The mixture was plated (200 µl per well) into 96-well plates (#3596, Costar, Cambridge, Mass.). Cultures were fed by removal and replacement of 50% of the volume of each well with fresh RPMI-hybrid-HAT every two to three days. Culture supernatants were assayed for the presence of anti-*P. aeruginosa* antibodies by enzyme-linked immunosorbant assay (ELISA) when the cell growth reached approximately 40% confluency in the wells, usually within 7–10 days.

The culture supernatants of the hybrid cells were assayed simultaneously on outer membrane preparations from each of the two immunizing bacteria. Outer membrane preparations were isolated by a modification of the method of Tam et al. (1982, *Infect. Immun.*, 36:1042–1053), which is incorporated herein by reference. Bacteria (*P. aeruginosa* Fisher immunotype 1 and Fisher immunotype 2) were inoculated into trypticase soy broth (TSB) and grown 16–18 hours at 34° C. with aeration in a gyratory shaker bath. The bacteria were harvested by centrifugation and washed twice with phosphate buffered saline (PBS, 0.14M NaCl, 3 mM KCl, 8 mM $Na_2HPO_4$-7 $H_2O$, 1.5 mM $KH_2PO_4$, PH 7.2) containing 150 trypsin inhibitory units (T.I.U.) aprotinin per ml (Sigma, St. Louis, Mo.).

The pellet from the final centrifugation was resuspended in 0.17M triethanolamine, 20 mM disodium ethylenediamine tetraacetic acid (EDTA), and then homogenized on ice for 10 minutes. The debris was pelleted from the homogenate at 14,900×g and discarded, and the supernatant was centrifuged again as above. The pellet was again discarded, and the membranes were pelleted from the supernatant by centrifugation at 141,000×g for one hour. The supernatant was discarded and the membrane pellets were stored overnight at 4° C. in 10 ml PBS containing 75 T.I.U. aprotinin per ml. The next day the pellets were resuspended by vortexing and then were aliquoted and stored at −70° C. The protein content of each was determined by the method of Lowry et al. (1951, *J. Biol. Chem.*, 193:265-275).

The antigen plates for the ELISA were prepared as follows. The outer membrane preparations were diluted to 5 μg per ml protein in PBS and 50 μl of the solutions were plated into each well of 96-well plates (Linbro #76-031-05, Flow Laboratories, Inc., McLean, Va.), sealed and incubated overnight at 37° C. Unbound antigen was flicked out of the plates and 100 μl of 5% (w/v) bovine serum albumin (BSA) in PBS was added to each well and the plates incubated for one hour at 37° C.

After flicking out the unadsorbed BSA, culture supernatants (50 μl) from each well of the fusion plates were replica-plated into the corresponding wells of antigen plates and incubated 30 minutes at 37° C. The unbound antibody was flicked out of the wells and the plates washed three times with 100 μl of 1% (w/v) BSA-PBS per well. Next, 50 μl per well of appropriately diluted biotinylated goat anti-mouse IgG (Tago, Inc., Burlingame, Calif.) was added to each well and incubated for 30 minutes at 37° C. The plates were washed three times as described above and then 50 μl of a preformed avidin:biotinylated horseradish peroxidase complex (Vectastain ABC Kit, Vector Laboratories, Inc., Burlingame, Calif.) prepared according to manufacturer's specifications was added to the wells. After 30 minutes at room temperature, the Vectastain reagent was flicked out of the wells, the wells were washed as above, and then 100 μl per well of substrate, o-phenylenediamine (0.8 mg/ml in 0.1M citrate buffer, pH 5.0, mixed with an equal volume of 0.03% [v/v] $H_2O_2$) was added. Substrate was incubated 30 minutes at room temperature in the dark, and the reactions were then terminated by the addition of 50 μl/well of 3N $H_2SO_4$.

Hybridoma cells secreting monoclonal antibodies that bound to either of the two antigen preparations were located by measuring the absorbance at 490 nm of the colorimetric reactions in each well on a Dynatech Model 580 MicroELISA reader (Alexandria, Va.). The cells in one well, designated Pa3 IVC2, produced antibody that bound to the Fisher immunotype 2 antigen plate only. This well was studied further as described below. The monoclonal antibody and clonal cell line from this well are both identified by the Pa3 IVC2 designation in the following text. Pa3 IVC2 cells from the master well were mini-cloned and cloned by limiting dilution techniques as described by Tam et al. (1982, *Infect. Immun.*, 36:1042-1053).

Ascites fluid containing high titred monoclonal antibody was prepared in CB6 $F_1$ mice (BALB/c [female]×C57BL/6 [male] $F_1$) according to procedures described by Tam et al. (1982, *Infect. Immun.*, 36:1042-1053). Two- to three-month-old male CB6 $F_1$ mice were injected intraperitoneally with 0.5 ml Pristane (2, 6, 10, 14-Tetramethylpentadecane, Aldrich Chemical Co., Milwaukee, Wisc.) 10-21 days prior to intraperitoneal injection with log phase Pa3 IVC2 cells in RPMI. Each mouse was injected with $0.5-1 \times 10^7$ cells in 0.5 ml. After approximately two weeks, the fluid that accumulated was removed from the mice every two to three days. The concentration of antibody in the ascites fluid was determined by agarose gel electrophoresis (Paragon, Beckman Instruments, Inc., Brea, Calif.) and all ascites that contained 5 mg/ml or greater antibody was pooled, aliquoted, and frozen at −70° C.

Characterization of the Molecular Target Bound by the Monoclonal Antibody

Culture supernatant from the cloned Pa3 IVC2 cell line was assayed by ELISA as described above on outer membrane preparations from all seven *P. aeruginosa* Fisher immunotype strains (A.T.C.C. 27312-27318), *P. aureofaciens* (A.T.C.C. 13985), and *Klebsiella pneumoniae* (A.T.C.C. 8047), all prepared as described above. Antibody Pa3 IVC2 bound to the outer membrane preparations of *P. aeruginosa* Fisher immunotypes 2, 6, and 7, and not to other Fisher immunotypes, *P. aureofaciens*, or *K. pneumoniae*.

The specific antigen identified by the antibody Pa3 IVC2 was identified by radioimmune precipitation. Briefly, this analysis entails incubating radiolabeled antigens with Pa3 IVC2 antibody and a particulate source of protein A which results in the formation of insoluble antibody:antigen complexes. These complexes are washed to remove any nonspecifically bound antigen and then the complexes are dissociated and separated in a polyacrylamide gel. The predominant radioactive species found in the gel are thereby identified as the corresponding antigen(s) to which the antibody Pa3 IVC2 binds.

Aliquots (25 μg) of soluble *P. aeruginosa* Fisher immunotypes 2, 3, 4, and 5 outer membrane preparations were radiolabeled in solid phase with $^{125}I$ using Iodogen (Pierce Chemical Co., Rockford, Ill.) (Fraker and Speck, 1978, *Biochem. Biophys. Res. Commun.*, 80:849-857; Markwell and Fox, 1978, *Biochemistry*, 17:4807-4817). This procedure resulted in the iodination of exposed tyrosine residues of most if not all proteins contained in the outer membrane preparations.

To diminish nonspecific binding of the outer membrane antigens to antibody Pa3 IVC2, the radiolabeled preparations ($5 \times 10^6$ counts per minute per assay) were first incubated for one hour at 4° C. with BALB/c normal mouse serum (1:40 final dilution). Pa3 IVC2 culture supernatant (0.5 ml) containing the Pa3 IVC2 antibody was then added to each outer membrane sample. After incubation of antigen and antibody for one hour at 4° C., the protein A source, IgGSORB (0.095 ml per sample) (The Enzyme Center, Inc., Boston, Mass.) was added and incubated for an additional 30 minutes at 4° C. (Kessler, S. W., 1975, *J. Immunol.*, 115:1617-1622). IgGSORB was prepared according to manufacturer's specifications, and just prior to use nonspecific reactions were prevented by blocking potentially reactive sites with culture media by washing the IgGSORB twice with RPMI-hybrid (RPMI-hybrid-HAT media excluding HAT).

The antigen-antibody-IgGSORB complexes were pelleted at 1500×g for ten minutes at 4° C., washed twice with phosphate-RIPA buffer (10 mM phosphate, pH 7.2, 0.15M NaCl, 1.0% [v/v] Triton X-100, 1.0% [w/v] sodium deoxycholate, 0.1% [w/v] sodium dodecyl sulfate [SDS], and 1.0% [v/v] aprotinin); twice with high salt buffer (0.1M Tris-HCl, pH 8.0, 0.5M LiCl, 1% [v/v] beta-mercaptoethanol); and once with lysis buffer (0.02M Tris-HCl, pH 7.5, 0.05M NaCl, 0.05% [v/v] Nonidet P-40) (Rohrschneider et al., 1979, Proc. Natl. Acad. Sci., U.S.A., 76:4479–4483. Antigen bound to the complex was released by incubation with sample buffer (0.125M Tris-HCl, pH 6.8, 2% [w/v] SDS, 2% [v/v] beta-mercaptoethanol, and 20% [v/v] glycerol) at 95° C. for ten minutes and collected in the supernatant after centrifugation at 1500×g for 10 minutes.

The supernatant samples were then applied to 14% polyacrylamide gels containing SDS prepared according to the method of B. Lugtenberg et al. (1978, FEBS Lett., 58:254–258) as modified by Hancock and Carey (1979, J. Bacteriol., 140:902–910, which is incorporated herein by reference), and the antigens were separated in the gel by electrophoresis overnight at 50 V constant voltage. Following fixation of the gel in 40% (v/v) methanol, 10% (v/v) acetic acid, and 5% (v/v) glycerol overnight, it was dried onto Whatman 3 MM paper via a Biorad gel dryer (Richmond, Calif.). The dried gel was covered with plastic wrap and exposed to Kodak X-AR film for 18 hours at room temperature.

Results of this experiment illustrated that Pa3 IVC2 bound to only one antigen in the outer membrane preparation of P. aeruginosa Fisher immunotype 2 only and not to any antigen present in the other outer membrane preparations. The molecular weight (MW) of the antigen in the gel was about 53,000 daltons as determined by comparing its mobility to that of $^{14}$C-labeled protein standards (phosphorylase B, 92,500 MW; BSA, 69,000 MW; ovalbumin, 46,000 MW; carbonic anhydrase, 30,000 MW; cytochrome C, 12,000 MW) (New England Nuclear, Boston, Mass.) that were separated in the same gel. The molecular weight of this antigen correlated with the molecular weight of flagellin, the protein comprising the flagella of P. aeruginosa, as reported by Montie et al. (1982, Infect. Immun., 35:281–288), which is incorporated herein by reference.

In addition, Pa3 IVC2 was examined by ELISA using P. aeruginosa Habs strains 1–12 (A.T.C.C. 33348–33359) that were fixed with ethanol to 96-well microtiter plates. The antigen plates were prepared as follows.

Overnight broth cultures of each organism were pelleted, washed twice with PBS and then resuspended in PBS to an $A_{660}$ of 0.2 O.D. units. The diluted bacteria were plated into wells (50 μl per well) and then centrifuged at 1500×g for 15 minutes at room temperature. The PBS was aspirated and then ethanol (95%) was added to the wells for 15 minutes at room temperature. After the ethanol was flicked out of the wells, the plates were air-dried and then covered and stored at 4° C. until use.

Results of the ELISA tests, performed as described above, showed that Pa3 IVC2 bound to ethanol-fixed Habs strains 2, 3, 4, 5, 7, 10, 11, and 12. This pattern of specificity indicated that Pa3 IVC2 bound to type b flagella of P. aeruginosa (Ansorg, R., 1978, Zbl. Bakt. Hyg., I. Abt. Orig. A, 242:228–238; Ansorg, R., et al., 1984, J. Clin. Microbiol., 20:84–88, both of which are incorporated herein by reference). Based upon this assignment of specificity to monoclonal Pa3 IVC2, the P. aeruginosa reference strains, Fisher immunotype 2, Fisher immunotype 6, and Fisher immunotype 7 bear type b flagella. From the preceding experimental data it has been concluded that Pa3 IVC2 binds specifically to P. aeruginosa flagellin type b.

In Vivo Protective Activity of Pa3 IVC2

Animal experiments were conducted to determine if monoclonal antibody PA3 IVC2 would protect a mouse challenged with multiple $LD_{50}$'s of live P. aeruginosa bacteria. The model chosen was the burned mouse model (Collins, M. S., and Roby, R. E., 1983, J. Trauma, 23:530–534, which is incorporated herein by reference). Groups of mice were given a serious burn according to the authors' protocol and then immediately challenged with 5–10 $LD_{50}$'s of Fisher immunotype 7. Monoclonal antibody was administered intraperitoneally as high titred ascites (0.2 ml intraperitoneally) prior to burn and challenge. No increase in number of survivors was observed in Pa3 IVC2 treated animals compared to those that did not receive antibody.

EXAMPLE 2

Example 2 demonstrates the methodology for the preparation of a murine hybridoma cell line producing a murine monoclonal antibody to P. aeruginosa flagellin type b that is protective in vivo.

Adult female BALB/c mice were first injected intraperitoneally with viable P. aeruginosa Fisher immunotype 6 (ATCC No. 27317) ($8 \times 10^6$ organisms) followed two weeks later with an injection of viable P. aeruginosa Fisher immunotype 5 (ATCC No. 27316) ($4 \times 10^6$ organisms). During the subsequent two-week period, viable P. aeruginosa Fisher immunotype 5 and Fisher immunotype 6 were administered together in two weekly injections. The dosage of each organism was increased such that the final dosage was ten-fold greater than the initial dosage. A final injection of P. aeruginosa Fisher immunotype 6 outer membrane preparations (50 μg protein) prepared according to the method of R. E. W. Hancock and H. Nikaido (1978, J. Bacteriol., 136:381–390) was given four days after the last viable bacteria injection. Three days after the last immunization, the spleen was removed from one mouse and the spleen cells prepared for hybridization as described in Example 1.

Culture supernatants of the hybridoma cells were assayed for the presence of anti-P. aeruginosa antibodies by ELISA on day 10 post-fusion according to the procedures stated in Example 1, except that the antigen for the ELISA plates was viable bacteria immobilized in the wells of the 96-well microtiter plates. The plates were prepared as follows.

Fifty microliters poly-L-lysine (PLL) (1 μg/ml in PBS) (Sigma #P-1524, St. Louis, Mo.) were added to each well of 96-well plates (Linbro) and incubated for 30 minutes at room temperature. Unadsorbed PLL was flicked out and the wells were washed three times with PBS. Bacterial cultures grown overnight in TSB were washed once with PBS and then resuspended in PBS to $O.D._{660nm}=0.2$. Fifty microliters of the bacterial suspensions were added to each well of the plate and allowed to bind at 37° C. for one hour. Unbound bacteria were removed by flicking the plates and then washing the wells three times with saline-Tween (0.9% [w/v] NaCl, 0.05% [v/v] Tween-20).

Nonspecific binding of the antibodies was blocked by the addition of 200 μl/well of blocking buffer (PBS containing 5% [w/v] non-fat dry milk, 0.01% [v/v] Antifoam A [Sigma, St. Louis, Mo.], and 0.01% [w/v] thimerosal) to the wells and incubation for one hour at room temperature. Excess blocking buffer was expelled and the wells were washed three times with saline-Tween as previously described.

Culture supernatants (50 μl) were replicaplated into the corresponding wells of the assay plates and incubated at room temperature for 30 minutes. The culture supernatants were removed by flicking the plates and washing the wells five times with saline-Tween.

An enzyme-conjugated second step antibody (horseradish peroxidase-conjugated goat anti-mouse IgG+IgM) (Tago, Inc., Burlingame, Calif.) was diluted in PBS containing 0.1% (v/v) Tween-20 and 0.2% (w/v) BSA according to previously determined titrations, and then 50 μl of the reagent was added to each well and incubated 30 minutes at room temperature. The excess reagent was expelled; the wells washed five times in saline-Tween; and 100 μl/well of o-phenylenediamine substrate was added and incubated for 30 minutes as described in Example 1. Reactions were terminated as stated in Example 1 and then read at $A_{490}$ nm on a Bio-Tek EL-310 Automated EIA Plate Reader.

By the above-described methods, the culture supernatants from the fusion were assayed for the presence of antibodies that bound to P. aeruginosa Fisher immunotypes 1, 2, 3, or 4, but not to control plates prepared by the same PLL and blocking procedure, but without bacteria. Supernatants containing antibody that bound to any of these four Fisher immunotypes were assayed a second time using each of the seven Fisher immunotype bacteria separately. Antibody present in the supernatant from one well, PaF4 IVE8, bound only to P. aeruginosa Fisher immunotypes 2, 6, and 7. Cells from well PaF4 IVE8 were cloned by limiting dilution methods as described in Example 1. The monoclonal antibody and the clonal cell line from this well are both identified by the PaF4 IVE8 designation in the following text. High titred monoclonal antibody-containing ascites fluid was generated as described in Example 1, except that BALB/c mice were used instead of CB6F$_1$.

Specificity of PaF4 IVE8

One assay performed to identify the antigen bound by monoclonal antibody PaF4 IVE8 was indirect immunofluorescence on bacterial organisms. Each of the seven reference Fisher immunotypes of P. aeruginosa, plus a nonflagellated strain of P. aeruginosa (PA103, A.T.C.C. 29260, Leifson, 1951, J. Bacteriol., 62:377–389), and Escherichia coli (G.S.C. A25) were grown overnight at 37° C. in TSB. The bacteria were pelleted by centrifugation and then washed twice in PBS. Each strain was resuspended in PBS to an O.D.$_{660nm}$=2.2.

The bacterial suspensions were then further diluted 1:150 and 20 μl samples were placed in individual wells of Carlson slides (Carlson Scientific Inc., Peotone, Ill.) and dried onto the slide at 40° C. Culture supernatants (25 μl) of PaF4 IVE8 were incubated on the dried bacterial samples on the slides in a humidified chamber at room temperature for 30 minutes. Unbound antibody was washed off the slides by dipping the slides in distilled water.

After the slides dried, fluorescein isothiocyanate (FITC)-conjugated goat anti-mouse IgG+IgM (25 μl per well of a 1:40 dilution in PBS) (Tago, Burlingame, Calif.) was incubated on the slides for thirty minutes at room temperature in a humidified chamber in the dark. The slides were again washed in distilled water, dried, and then covered with a coverslip mounted with glycerol in PBS (9:1). Slides were viewed with a fluorescence microscope.

Fluorescent staining was observed only on P. aeruginosa Fisher immunotypes 2, 6, and 7, and was observed to be a sinusoidal pattern (line) emanating from one end only of the organisms. This is consistent with the morphology and location of the single polar flagellum of these bacteria.

The reaction of PaF4 IVE8 with flagella was confirmed by immunoblot analysis. Outer membrane antigens from P. aeruginosa Fisher immunotype 6 (see Example 1) were separated by electrophoresis in a 14% polyacrylamide gel containing SDS as described in Example 1, except that electrophoresis was run for five hours at 80 mAmps constant amperage. Prestained molecular weight markers (lysozyme, 14,300 MW; beta-lactoglobulin, 18,400 MW; alpha-chymotrypsinogen, 25,700 MW; ovalbumin, 43,000 MW; bovine serum albumin, 68,000 MW; phosphorylase B, 97,400 MW; and myosin, 200,000 MW) (BRL, Gaithersburg, Md.) were included in the same polyacrylamide gel.

Antigens were transferred from the polyacrylamide gel to a nitrocellulose membrane, (NCM), (0.45 μm, Schleicher & Schuell, Inc., Keen, N.H.) in a Tris-glycine-methanol buffer (Towbin et al. [1979], Proc. Natl. Acad. Sci., U.S.A., 76:4350–4354) containing 0.05% (w/v) SDS overnight at 4° C. at a constant amperage of 200 mA. After transfer, the NCM was incubated in 0.05% (v/v) Tween-20 in PBS (PBS-Tween) (Batteiger, B., et al., 1982, J. Immunol. Meth., 55:297–307) for one hour at room temperature. For this step and all subsequent steps, the tray containing the NCM was placed on a rocking platform to ensure distribution of solution over the entire NCM.

After one hour, the PBS-Tween solution was poured off and PaF4 IVE8 ascites (diluted 1:1000 in PBS-Tween) was added and incubated with the NCM for one hour at room temperature. The NCM was then washed five times, five minutes each, with PBS-Tween, to remove unbound antibody. Alkaline phosphatase-conjugated goat anti-mouse IgG+IgM (Tago, Inc.) was diluted according to manufacturer's specifications and incubated with the NCM for one hour at room temperature. The NCM was washed five times as described above, and the substrate containing bromochloroindolyl phosphate and nitroblue tetrazolium (Sigma, St. Louis, Mo.), prepared as described by Leary et al. (1983, Proc. Natl. Acad. Sci., U.S.A., 80:4045–4049), was added and incubated 10–20 minutes at room temperature. The reaction was terminated by washing substrate away with distilled water.

The results of this experiment showed that PaF4 IVE8 bound specifically to a single antigen with a molecular weight of 53,000 daltons in the outer membrane preparation. The results of the indirect immunofluorescence assay and immunoblotting demonstrate that PaF4 IVE8 binds to the flagella of P. aeruginosa.

The flagella type that PaF4 IVE8 recognized was determined by ELISA. Habs strains 1-12 (A.T.C.C. #33348-33359) were each bound to wells of 96-well micro-titer plates (Linbro) with PLL, and the ELISA performed as described earlier in this Example. The source of PaF4 IVE8 antibody was culture supernatant. Positive reactions were noted in wells containing Habs strains 2, 3, 4, 5, 7, 10, 11, and 12, thus indicating that PaF4 IVE8 binds to type b flagella. The in vivo protection data are presented below in Example 4.

EXAMPLE 3

Example 3 demonstrates the methodology for the preparation of a murine hybridoma cell line producing a monoclonal antibody, reactive with anti-*P. aeruginosa* flagella type a, that is protective in vivo.

The lymphoid cell source for the fusion was a spleen from an immunized BALB/c mouse that had been injected four times intraperitoneally over a six-week period with purified type a flagella (10–20 μg protein) from Habs strains 6 and 8 (A.T.C.C. #33353 and 33355). Flagella were purified according to the method T. C. Montie et al. (1982, *Infect. Immun.*, 35:281–288, which is incorporated herein by reference) with the exception that the final centrifugation of flagella was at 100,000×g for one hour rather than 40,000×g for three hours. A second modification adopted for some procedures was to shear the flagella from the bacteria 30 seconds in a blender rather than three minutes. (Allison et al., 1985, *Infect. Immun.*, 49:770–774).

Protein concentrations of each preparation were determined with the Bio-Rad Protein Assay (Bio-Rad. Richmond, Calif.) and the presence of contaminating lipopolysaccharide (LPS) was assessed by measuring the KDO content (Karkhanis, Y. D., et al., 1978, *Anal. Biochem.*, 85:595–601). The molecular weights of the flagella proteins were determined by comparing their migration in an SDS polyacrylamide gel with the migration of standard protein markers (BRL) (see Example 2). The molecular weight of Habs 6 flagellin was 51,700 daltons and that of Habs 8 flagellin was 47,200 daltons. These values agree with those obtained by J. S. Allison et al. (1985, *Infect. Immun.*, 49:770–774, which is incorporated herein by reference).

Fusion of splenocytes from flagellin-immunized mice and NS-1 myeloma cells was performed three days after the last immunization, as described in Examples 1 and 2. When hybridoma cells grew to approximately 40% confluency (day 7), culture supernatants were replica-plated into corresponding wells of three different antigen plates, PLL-bound *P. aeruginosa* Fisher immunotype 1 (see Example 2 for preparation), and formalin-fixed Habs 6 and Habs 9.

The bacteria for the formalin-fixed antigen plates were grown, washed, and diluted as described for PLL-bound antigen plates. Diluted bacteria (0.2 O.D. units at $A_{660}$) were added to individual wells (50 μl per well) of Linbro 96-well micro-titer plates and the plates were then centrifuged at 1200×g for 20 minutes at room temperature. The supernatants were flicked out of the wells and 75 μl of 0.2% (v/v) formalin in PBS was added to each well and incubated for 15 minutes at room temperature. After the formalin was flicked out of the wells, the plates were air-dried and stored at 4° C. until used. Formalin did not alter antigenicity of the flagella as shown by the ability of anti-flagella antisera to agglutinate formalin-treated organisms (Lanyi, B., 1970, Acta Microbiol. Acad. Sci., Hung., 17:35–48). *P. aeruginosa* Fisher immunotype 1 strain was included as a control because this strain was nonflagellated, as shown by mordant dye staining (*Manual of Clin. Microbiol.*, 1985, Lennette, ed. Amer. Soc. Microbiol., Washington, D.C., p. 1099). Hybrid cells in the well designated FA6 IIG5 produced an antibody that bound to Habs 6 and Habs 9 (both flagella type a bearing strains) but not Fisher immunotype 1.

Cells from well FA6 IIG5 were subcultured and cloned as described in previous examples. The monoclonal antibody and the clonal cell line from this well are both identified by the FA6 IIG5 designation in the following text. Ascites was produced in BALB/c mice as described in Example 2.

Specificity of FA6 IIG5

The specificity of the antibody FA6 IIG5 was determined by indirect immunofluorescence and immunoblotting. Indirect immunofluorescence was performed essentially as described in Example 2, with the following modifications.

Bacteria cultures grown overnight on trypticase soy agar at 30° C. were removed from the plates with cotton swabs and resuspended in PBS to an $A_{660}$ of 0.2 O.D. units. Formalin (0.37% [v/v] in PBS final concentration) was added to the suspension with vortexing. After an incubation at room temperature for 15 minutes, the bacteria were diluted 1:12 in PBS and 20 μl of this suspension was placed in individual wells of Carlson slides. After drying, the slides were prepared for viewing as described in Example 2. The source of antibody was culture supernatant from the FA6 IIG5 cell line.

Fluorescent staining by the FA6 IIG5 antibody was observed only with *P. aeruginosa* strains bearing type a flagella and none of those bearing type b. The fluorescence pattern observed was a sinusoidal line pattern indicating that FA6 IIG5 bound to the flagella. The fluorescent signal was enhanced by treating the bacteria with formalin, but the treatment was not required to visualize flagellar staining with the antibody.

Immunoblotting was performed as described in Example 2. The sources of flagella type a antigens were the purified flagellar preparations (see this Example). Antigens were separated in 10% polyacrylamide gels containing SDS (Laemmli, U. K., 1970, *Nature* [London], 227:680–685) and transferred to an NCM. Preparations of FA6 IIG5, either culture supernatant or ascites diluted 1:1000, were reacted with the NCM, and the reaction detected with an appropriate enzyme-conjugated reagent and enzyme substrate as described in Example 2. The immunoblot illustrated that FA6 IIG5 bound specifically to the 51,700 MW flagellin of Habs 6 and the 47,200 MW flagellin of Habs 8.

Confirmation that FA6 IIG5 reacted with only flagella type a and not type b was obtained by ELISA, in which Habs strains 1–12 were bound individually with PLL to the wells of Linbro 96-well microtiter plates. The antibody bound to only Habs strains 1, 6, 8, and 9, which are the only flagella type a bearing strains of the twelve (see, Ansorg, R., et al., 1984, *J. Clin. Microbiol.*, 20:84–88, which is incorporated herein by reference). In vivo protection studies are presented in the following Example 4.

EXAMPLE 4

Example 4 demonstrates protection of mice passively immunized with antibodies PaF4 IVE8 and FA6 IIG5 against challenge with *P. aeruginosa* in the burned mouse model.

The anti-flagella monoclonal antibodies were tested in the burned mouse model according to the method of M. S. Collins and R. E. Roby (1983, *J. Trauma*, 23:530–534, which is incorporated herein by reference). For the protection studies, all antibodies were purified by protein A-Sepharose chromatography (Ey, P. L., et al., 1978, *Immunochemistry*, 15:429–436, which is incorporated herein by reference) and dialyzed into PBS buffer. The flagella type a bearing strain used in the animal trials was *P. aeruginosa* PA220 (from Dr. James Pennington, Boston, Mass.) and the flagella type b strain was the reference *P. aeruginosa* Fisher immunotype 2 (A.T.C.C. #27313).

Forty micrograms of purified monoclonal antibody was given per mouse intravenously one to two hours prior to burn and challenge. Immediately after the burn, the animals received 0.5 ml cold PBS subeschar containing the challenge bacteria. The challenge dose was approximately 10 $LD_{50}$'s for each organism. The results of the animal trials are presented in Tables I and II.

TABLE I

Protection Study of an Anti-Flagela Type a Monoclonal Antibody in the Burned Mouse Model[1]

| Treatment | Percent Survival by Day[2] | | | | | | | | |
|---|---|---|---|---|---|---|---|---|---|
| | 1 | 2 | 3 | 4 | 5 | 6 | 7 | 8 | 9 |
| Anti-Flagella a, FA6 IIG5 | 100 | 100 | 100 | 100 | 100 | 90 | 90 | 80 | 80 |
| Anti-Flagella b, PaF4 IVE8 | 100 | 20 | 10 | 10 | 10 | 10 | 10 | 10 | 10 |
| Non-specific anti-LPS monoclonal antibody | 100 | 40 | 30 | 20 | 10 | 10 | 10 | 10 | 10 |
| PBS, no bacteria | 80 | 80 | 80 | 80 | 80 | 80 | 80 | 80 | 80 |

[1]Mice were challenged subeschar with approximately 10 $LD_{50}$'s of *P. aeruginosa* PA220.
[2]The percent is based upon survival of mice in ten animal groups with the exception of the PBS only control group which consisted of five mice. Days are post-burn and challenge.

TABLE II

Protection Study of Anti-Flagella Type b Monoclonal Antibody in the Burned Mouse Model[1]

| Treatment | Percent Survival by Day[2] | | | | | | | | |
|---|---|---|---|---|---|---|---|---|---|
| | 1 | 2 | 3 | 4 | 5 | 6 | 7 | 8 | 9 |
| Anti-Flagella b, PaF4 IVE8 | 100 | 100 | 90 | 90 | 90 | 90 | 90 | 90 | 90 |
| Anti-Flagella a, FA6 IIG5 | 100 | 20 | 10 | 10 | 10 | 10 | 10 | 10 | 10 |
| Non-specific anti-LPS Monoclonal antibody | 100 | 20 | 20 | 20 | 20 | 20 | 20 | 20 | 20 |
| PBS, no bacteria | 100 | 100 | 100 | 100 | 100 | 100 | 100 | 100 | 100 |

[1]Mice were challenged subeschar with approximately 10 $LD_{50}$'s of *P. aeruginosa* Fisher immunotype 2.
[2]Percent survival was based on number of mice surviving per group of ten with the exception of the PBS only control group, which consisted of five mice. Days are post-burn and challenge.

Very significant survival was observed in mice that were treated with the anti-a antibody or anti-b antibody and then challenged with the corresponding antigen. Conversely, 80-90% of the untreated but challenged mice or animals treated with a nonmatching antiflagellar monoclonal antibody or nonspecific anti-LPS antibody died. The inability of the antiflagella type a antibody to protect mice from a lethal challenge of flagella type b bearing *P. aeruginosa* Fisher immunotype 2, and the inability of the antiflagella type b antibody to protect mice from a lethal challenge of type a bearing *P. aeruginosa* PA220, corroborated in vivo the specificity of the antibodies observed in vitro. Survival of mice burned, but not infected, indicated that the burn itself was not lethal.

EXAMPLE 5

Example 5 demonstrates the extensive cross-reactivity of PaF4 IVE8 and FA6 IIG5 with *P. aeruginosa* clinical isolates, indicating the clinical utility of these antibodies in immunotherapy of *P. aeruginosa* infections.

Clinical isolates were obtained from hospitals and clinics. The isolates were from a variety of isolation sites, including blood, wounds, respiratory tract, urine, and ears. A total of 157 isolates were examined.

PaF4 IVE8 bound specifically to 34 clinical isolates (22%), while the flagella type a antibody, FA6 IIG5, bound to 102 clinical isolates (65%), for a total of 136 of 157 isolates (87%). Of the 21 strains that were not recognized by either antibody, 19 were nonflagellated as shown by mordant dye staining. Therefore, both antibodies in combination bound to 136 of 138 (98%) of flagellated clinical isolates, confirming prior reports (see, R. Ansorg, 1978, Zbl. Bakt. Hyg., I Abt. Orig. A, 242:228-238, which is incorporated herein by reference).

EXAMPLE 6

Example 6 demonstrates methods for the production of human monoclonal antibodies that bind to *P. aeruginosa* type b flagella.

A peripheral blood sample from an individual immunized with a high molecular weight polysaccharide preparation (Pier et al., 1984, *Infect. Immun.*, 45:309) served as a source of B cells. Mononuclear cells were separated from the blood by standard centrifugation techniques on Ficoll-Paque (Boyum (1968) *Scand. J. Clin. Lab. Invest.*, 21:77) and washed twice in calcium/magnesium-free phosphate buffered saline (PBS).

The mononuclear cells were depleted of T-cells using a modified E-rosetting procedure. Briefly, the cells were first resuspended to a concentration of $1 \times 10^7$ cells/ml in PBS containing 20% fetal calf serum (FCS) at 4° C. One ml of this suspension was then placed in a 17×100 mm polystyrene round-bottom tube to which was added $1 \times 10^9$ 2-amino-isothiouronium bromide (AET)-treated sheep red blood cells from a 10% (v/v) solution in Iscove's modified Dulbecco's medium (Iscove's medium) (Madsen and Johnson (1979) *J. Immun. Methods*, 27:61). The suspension was very gently mixed for 5-10 minutes at 4° C. and the E-rosetted cells then removed by centrifugation on Ficoll-Paque for 8 minutes at 2500×g at 4° C. E-rosette negative peripheral blood mononuclear cells (E−PBMC) banding at the interface were collected and washed once in Iscove's medium and resuspended in same containing 15% (v/v) FCS, L-glutamine (2 mmol/l), penicillin (100 IU/ml), streptomycin (100 μg/ml), hypoxanthine ($1 \times 10^{-4}$ M), aminopterin ($4 \times 10^{-7}$ M) and thymidine ($1.6 \times 10^{-5}$ M). This medium is hereafter referred to as HAT-medium.

Cell-driven transformation of the E−PBMC was accomplished by co-cultivating these cells with a transforming cell line. The transforming cell line was an Epstein-Barr nuclear antigen (EBNA) positive human lymphoblastoid cell line derived by ethyl methane-sulphonate (EMS) mutagenesis of the GM 1500 lymphoblastoid cell line followed by selection in the presence of 30 μg/ml 6-thioguanine to render the cells hypoxanthine-guanine phosphoribosyl transferase (HGPRT) deficient and thus HAT sensitive. This cell line is denominated the 1A2 cell line and was deposited at the American Type Culture Collection (A.T.C.C.) on Mar. 29, 1982, under A.T.C.C. No. CRL 8119. 1A2 cells in logarithmic growth phase were suspended in HAT-medium and then combined with the E−PBMC's at a ratio of fifteen 1A2 cells per PBMC. The cell mixture was plated into thirty round-bottom 96-well microtiter plates (Costar 3799) at a concentration of 32,000 cells/well in a volume of 200 μl per well, and incubated at 37° C. in a humidified atmosphere containing 6% $CO_2$. Cultures were fed on days 5 and 8 post-plating by replacement of half the supernatant with fresh HAT-medium. Sixteen days after plating, 100% of the wells contained proliferating cells and in most of the wells the cells were of sufficient density for removal and testing of supernatants for anti-*P. aeruginosa* antibodies.

Supernatants were screened for the presence of anti-*P. aeruginosa* antibodies using the ELISA technique as described in Example 2 with the following modifications. A pool of the seven Fisher immunotype reference strains (A.T.C.C. Nos. 27312–27318) ($A_{660}$=0.2 O.D. units) were bound to flat-bottom 96-well microtiter plates (Immulon II, Dynatech) pre-treated with poly-L-lysine, incubated, and washed as described in Example 2. After blocking non-specific binding sites and washing the plates, 50 μl of PBS containing 0.1% (v/v) Tween-20 and 0.2% (w/v) BSA was added per well. Culture supernatants (50 μl) were then replica-plated into the corresponding wells of assay plates and into control plates that were treated with PLL and blocked, but did not contain bacteria. After incubation and washing, enzyme-conjugated second step antibodies (50 μl per well), horseradish peroxidase-conjugated goat anti-human IgG and goat anti-human IgM, diluted appropriately in PBS containing 0.1% (v/v) Tween-20 and 0.2% (w/v) BSA, were added to the wells and the assay completed as described in Example 2.

Supernatants containing antibody that bound to the pool of Fisher immunotypes, but not to the control plate, were assayed a second time using each of the seven Fisher immunotype bacteria separately. Antibody present in the supernatant from one well, 20H11, bound only to *P. aeruginosa* Fisher immunotypes 2, 6, and 7. The cells were subcultured repeatedly at decreasing low cell densities until all wells with growth were secreting antibody. The cell line and the monoclonal antibody are both identified by the 20H11 designation in the following text.

A second transformation was performed in which the source of B cells was from the peripheral blood of a cystic fibrosis patient known to have had a chronic *P. aeruginosa* infection. E−PBMC's were prepared as described above and co-cultivated with the transforming cell line, 1A2, at a ratio of 72 1A2 cells per E−PBMC. The cell mixture was plated into fifteen round-bottom 96-well microtiter plates at a concentration of $7.4 \times 10^4$ cells per well and cultured as above.

Supernatants were assayed by ELISA for the presence of anti-*P. aeruginosa* antibodies sixteen days after the transformation was plated. The assay was performed as described for the previous transformation, except that the pool of *P. aeruginosa* strains used for the initial screening was composed of Fisher immunotype reference strains, F2, F4, F6, and F7 (A.T.C.C. Nos. 27313, 27315, 27316, and 27317), and three clinical isolates from the Genetic Systems Corporation Organism Bank (GSCOB) that had different LPS immunotypes and flagella types. The clinical isolate PSA I277 (GSCOB) bears type a flagella and Fisher immunotype 1 LPS; the second isolate PSA G98 (GSCOB) bears type a flagella and Fisher immunotype 3 LPS; and the third, PSA F625 (GSCOB), bears type b flagella and Fisher immunotype 5 LPS. This mixture of reference strains and clinical isolates will be referred to as the *P. aeruginosa* flagellated pool. Supernatants containing antibody that bound to plates containing the *P. aeruginosa* flagellated pool, but not to the PLL-coated control plates, were assayed by ELISA a second time on the individual strains of the pool. One well, 3C1, bound to reference strains F2, F6, and F7 and to the clinical isolate F625.

Cloning of the 3C1 cell line was accomplished by first subculturing the cells in two rounds of low density subculture, first at 20 cells per well of 96-well plates followed by culturing at 2 cells per well. Formal cloning of the specific antibody-producing cells was performed by plating the cells at a density of about 1 cell/well in 72-well Terasaki plates (Nunc #1-36538) in a volume of 10 μl/well of HAT-medium lacking the aminopterin component (HT-medium). The plates were placed in an incubator for 2–3 hours to allow the cells to settle to the bottom of the wells and were then microscopically scored by two individuals for wells that contained a single cell. The wells were fed daily with HT-medium and when outgrowth was sufficient, the cells were transferred to a 96-well round-bottom plate. All wells with outgrowth were assayed by ELISA on *P. aeruginosa* strains bearing type b flagella, and all were found to be producing the appropriate antibody. The cell line and the monoclonal antibody are both identified by the 3C1 designation in the following text.

The antigen identified by 20H11 and 3C1 was flagella as shown by indirect immunofluorescence and immunoblotting. The techniques were performed basically as described in Examples 2 and 3. For the indirect immunofluorescence assay *P. aeruginosa* strains bearing type b flagella, reference Fisher immunotypes F2, F6, and F7 (A.T.C.C. Nos. 27313, 27317, and 27318) and a strain bearing type a flagella, reference Fisher immunotype 4 (A.T.C.C. No. 27315), were prepared as described in Example 3. The flagella type of the reference strains was determined by typing with the murine monoclonal antibodies, PaF4 IVE8 and FA6 IIG5. The slides were prepared for viewing as described in Example 2. The sources of both antibodies were culture supernatants, and the FITC-conjugated reagent was FITC-conjugated goat anti-human Ig (polyvalent) (Tago, Burlingame, Calif.) diluted 1:100 in PBS containing 0.5% (w/v) bovine gamma globulins (Miles Scientific, Cat. No. 82-041-2, Naperville, IL) and 0.1% (w/v) sodium azide as a preservative.

Fluorescent staining by the 20H11 and 3C1 antibodies was observed only with *P. aeruginosa* strains bearing type b flagella and not with the flagella type a bearing strain, reference Fisher immunotype 4. The fluorescence pattern observed was a sinusoidal line pattern emanating from one end of the bacteria indicating that the antibodies bound to the flagella of the bacteria.

Immunoblotting was performed as described in Example 2. Purified type b flagella from the *P. aeruginosa* reference strains Fisher immunotype 2 (A.T.C.C. No. 27313), and purified flagella type a from reference strains Habs 6 and Habs 8 (A.T.C.C. Nos. 33353 and 33355) were prepared as described in Example 3. Antigens were separated in a 10% polyacrylamide gel (see Example 3) and transferred to an NCM. Culture supernatants containing 20H11 or 3C1 antibodies, culture supernatant containing a non-specific human antibody, and culture media were incubated with the NCM and the reaction detected with an alkaline phosphatase conjugated goat anti-human Ig (polyvalent) (Tago, Burlingame, Calif.) diluted in PBS containing 0.05% (v/v) Tween-20. Enzyme substrate was prepared as described in Example 2. The immunoblot illustrated that both antibodies bound to the 53,000 MW flagellin protein of Fisher immunotype 2, and not to the 51,700 MW flagellin protein of Habs 6 nor to the 47,200 MW flagellin protein of Habs 8. No reaction was observed with either the non-specific human antibody or the culture media.

Additional confirmation that antibodies 20H11 and 3C1 bound only to type b flagella and not to type a was obtained by ELISA, in which Habs strains 1–12 were bound individually with PLL to the wells of Immulon 96well microtiter plates. The antibodies bound only to Habs strains 2, 3, 4, 5, 7, 10, 11,and 12, which are type b bearing strains (Ansorg et al. (1984) *J. Clin. Microbiol.*, 20:84).

EXAMPLE 7

Example 7 demonstrates methods for the production of a human monoclonal antibody that binds to *P. aeruginosa* type a flagella.

A peripheral blood sample from an individual immunized with a high molecular weight polysaccharide preparation (Pier et al. (1981) *Infect. Immun.*, 34:461) served as a source of B cells. The mononuclear cells were separated from the blood and then depleted of T-cells as described in Example 6. The cells were then frozen in FCS containing 10% dimethly sulfoxide in a liquid nitrogen vapor tank. At a later date the cells were thawed quickly at 37° C., washed once in Iscove's medium and resuspended in HAT-medium. Cell-driven transformation was accomplished by co-cultivating the E−PBMC's with 1A2 cells at a ratio of 30 1A2 cells per E−PBMC. The cell mixture was plated into 30 96-well tissue culture plates at a concentration of 62,000 cells per well. Cultures were fed the seventh day after plating by replacement of half the volume with HAT-medium. Cell proliferation was observed in 100% of the wells on the fourteenth day post-plating, and supernatants were removed from the wells and assayed at this time.

Supernatants were assayed by ELISA for the presence of anti-*P. aeruginosa* antibodies by using the flagellated *P. aeruginosa* pool and PLL-treated plates as a control, as described in Example 6. Supernatants containing antibodies that bound to the flagellated pool, but not to the PLL control plates, were assayed again on the individual bacteria strains of the flagellated pool. One well, 21B8, contained antibody that bound to PSA I277, PSA G98, and reference Fisher immunotype 4, which are the three strains of the flagellated pool that bear type a flagella.

Cloning of the 21B8 cell line was accomplished as described in Example 6 for the 3C1 cell line with the following modifications at the formal cloning step. After the wells of the Terasaki plates were scored for the presence of only a single cell, each cell was transferred from the Terasaki plate to an individual well of a 96-well round-bottom culture plate in a volume of 100 μl HAT-medium lacking the aminopterin component (HT-medium). Non-transforming, HAT-sensitive lymphoblastoid cells were included in all wells at a density of 500 cells/well as feeder cells. Five days post-plating, 100 μl of HAT-medium was added to the wells to selectively kill the feeder cells. Wells were again fed on days 7 and 9 post-plating by replacement of half the supernatant with HAT-medium. The cells were then fed with HT-medium until the cells were of sufficient density to detect the presence of antibody by ELISA. All wells with outgrowth produced antibody that bound to flagella type a bearing *P. aeruginosa* strains. The cell line and the monoclonal antibody are both identified by the 21B8 designation in the following text.

The antigen identified by 21B8 was flagella as shown by indirect immunofluorescence and immunoblotting (see Example 6 for descriptions of the techniques). Fluorescent staining by the 21B8 antibody was observed only with *P. aeruginosa* reference strain Fisher immunotype 4 (A.T.C.C. No. 27315), which bears a type a flagella, and not with *P. aeruginosa* reference strain immunotype 2 (A.T.C.C. No. 27313) that bears type a flagella. The fluorescence pattern observed was a sinusoidal line pattern emanating from one end of the bacteria indicating that the antibody bound to the flagella of the bacteria.

Immunoblotting was performed as described in Example 2. Purified type a flagella from the *P. aeruginosa* reference strain Habs 6 (A.T.C.C. No. 33353) and purified flagella type b from the *P. aeruginosa* reference strain Fisher immunotype 2 (A.T.C.C. No. 27313) were prepared as described in Example 3. Antigens were separated in a 10% polyacrylamide gel (see Example 3) and transferred to an NCM. Culture supernatants containing either 21B8 or a non-specific human antibody and culture media were reacted with the NCM and the reaction detected with an alkaline phosphatase-conjugated goat anit-human Ig (polyvalent) and enzyme substrate as described in Examples 2 and 6. The immunoblot illustrated that the 21B8 antibody bound only to the 51,700 MW flagellin protein of Habs 6 and not to the 53,000 MW flagellin protein of Fisher immunotype 2. No reaction was observed with either the non-specific human antibody or the culture media.

EXAMPLE 8

Example 8 demonstrates protection of mice passively immunized with human anti-flagella antibodies, 20H11, 3C1, and 21B8, against challenge with *P. aeruginosa* in the burned mouse model.

The human anti-flagella monoclonal antibodies were tested in the burned mouse model (see Example 4). 21B8 and 20H11 antibodies were prepared by precipitation of culture supernatants generated from the respective cell lines with ammonium sulfate (50% final concentration) (Good et al., *Selected Methods in Cellular Immunology*, Mishell, B. B., and Shiigi, S. M., eds., W. J. Freeman & Co., San Francisco, Calif., 1980, 279–286). The precipitate was solubilized in PBS, dialyzed against PBS overnight at 4° C., and then sterile filtered prior to administration in animals. The source of antibody 3C1 and the non-specific anti-LPS antibody used as a negative control in that study was culture supernatant. As a positive control for each study, the appropriate purified murine monoclonal antibody, PaF4 IVE8 or FA6 IIG5, was included.

The flagella type a bearing strain used in the animal trials was the clinical isolate PSA A522 (GSCOB), which expresses Fisher immunotype 1 LPS, and the flagella type b strain was clinical isolate PSA A447 (GSCOB), which expresses Fisher immunotype 6 LPS. The human antibodies (0.45 ml) were premixed with the bacteria (greater than 5 $LD_{100}$'s in 0.05 ml) and inoculated subeschar immediately after the burn was administered. The results of the animals' trials are presented in Tables III, IV, and V.

TABLE III

Protection Study of the Human Anti-Flagella Type a[1] Monoclonal Antibody 21B8 in the Burned Mouse Model

| Treatment | Percent Survival by Day[2] | | | | | | | | |
|---|---|---|---|---|---|---|---|---|---|
| | 1 | 2 | 3 | 4 | 5 | 6 | 7 | 8 | 9 |
| Murine anti-flagella a, FA6 IIG5[3] | 100 | 100 | 100 | 100 | 88 | 88 | 88 | 88 | 88 |
| Human anti-flagella a, 21B8 | 100 | 100 | 100 | 100 | 100 | 100 | 100 | 100 | 100 |
| Human anti-flagella b, 20H11 | 100 | 0 | 0 | 0 | 0 | 0 | 0 | 0 | 0 |
| PBS | 100 | 25 | 12 | 12 | 12 | 12 | 12 | 12 | 12 |

[1]Mice were challenged subeschar with greater than 5 $LD_{100}$'s of *P. aeruginosa* PSA A522.
[2]Percent survival was based on the number of mice surviving per group of eight animals. Days are post-burn and challenge.
[3]Purified antibody (10 μg in 0.45 ml PBS) was pre-mixed with the bacteria and administered subeschar after burn and challenge.

TABLE IV

Protection Study of the Human Anti-Flagella Type b Monoclonal Antibody 20HII in the Burned Mouse Model[1]

| Treatment | Percent Survival by Day[2] | | | | | | | | |
|---|---|---|---|---|---|---|---|---|---|
| | 1 | 2 | 3 | 4 | 5 | 6 | 7 | 8 | 9 |
| Murine anti-flagella b, PaF4 IVE8[3] | 100 | 100 | 100 | 100 | 100 | 100 | 100 | 100 | 100 |
| Human anti-flagella b, 20H11 | 100 | 100 | 100 | 100 | 100 | 100 | 100 | 100 | 100 |
| Human anti-flagella a, 21B8 | 100 | 0 | 0 | 0 | 0 | 0 | 0 | 0 | 0 |
| Media | 80 | 0 | 0 | 0 | 0 | 0 | 0 | 0 | 0 |

[1]Mice were challenged subeschar with greater than 5 $LD_{100}$'s of *P. aeruginosa* clinical isolate, PSA A447.
[2]Percent survival was based on the number of mice surviving per group of five animals. Days are post-burn and challenge.
[3]Purified antibody (10 μg in 0.45 ml PBS) was pre-mixed with the bacteria and administered subeschar after burn and challenge.

TABLE V

Protection Study of the Human Anti-Flagella Type b Monoclonal Antibody 3Cl in the Burned Mouse Model[1]

| Treatment | Percent Survival by Day[2] | | | | | | | | |
|---|---|---|---|---|---|---|---|---|---|
| | 1 | 2 | 3 | 4 | 5 | 6 | 7 | 8 | 9 |
| Murine anti-flagella b, PaF4 IVE8[3] | 100 | 100 | 100 | 100 | 100 | 100 | 100 | 100 | 100 |
| Human anti-flagella b, 3Cl | 100 | 100 | 80 | 80 | 80 | 80 | 80 | 80 | 80 |
| Non-specific anti-LPS monoclonal antibody | 100 | 0 | 0 | 0 | 0 | 0 | 0 | 0 | 0 |

[1]Mice were challenged subeschar with greater than 5 $LD_{100}$'s of PSA A447.
[2]Percent survival was based on survival of mice in five animal groups. Days are post-burn and challenge.
[3]Purified antibody (40 μg) was administered intravenously two hours prior to burn and challenge.

Very significant survival was observed in mice that were treated with the anti-flagella type a antibody, or either of the two anti-flagella type b antibodies, and then challenged with the corresponding antigen. Conversely, 88%–100% of the untreated but challenged mice, or those treated with a nonmatching anti-flagellar monoclonal antibody or nonspecific anti-LPS antibody, died. As was observed with the murine monoclonal antibodies (see Example 4), the human antiflagella antibodies specifically protect against lethal challenge only with the organisms bearing the corresponding flagella type, i.e., the human anti-flagella type a antibody provided protection against lethal challenge with the flagella type a bearing organism and not the type b, and the anti-flagella type b antibodies protected mice that were challenged with flagella type b bearing strains, but not the type a bearing organism.

EXAMPLE 9

Example 9 demonstrates the cross-reactivity of the human anti-flagella antibodies 20H11, 3C1, and 21B8 with *P. aeruginosa* clinical isolates.

*P. aeruginosa* clinical isolates (114) obtained from hospitals and clinics and isolated primarily from burn wounds and blood were identified as bearing flagella type a or type b by typing with the murine monoclonal antibodies, FA6 IIG5 or PaF4 IVE8 (see Examples 2, 3, and 5). Fifty-five of the clinical isolates were identified as bearing type a flagella by reacting with the murine monoclonal antibody, FA6 IIG5, and 59 were identified as type b bearing by their reaction with the murine monoclonal antibody, PaF4 IVE8.

Cross-reactivity of the anti-flagella type a human monoclonal antibody, 21B8, was extensive in that the antibody recognized 52 of the 55 flagella type a bearing clinical isolates (95%). Cross-reactivity of 20H11 with the isolates bearing type b flagella was also extensive in that 20H11 recognized all 59 isolates (100%). In contrast, the other anti-flagella type b monoclonal antibody, 3C1, bound to only 43 of the 59 isolates (73%). These results demonstrate that 20H11 binds to a pan-reactive epitope (i.e., an epitope present on at least about 90%–95% of flagellated *P. aeruginosa* strains), whereas 3C1 binds to an epitope not present on all type b flagellin molecules. Even though the flagella type b antigen is serologically uniform when analyzed with polyclonal antisera (Lanvi, B., supra, and Ansorg, R., supra), the cross-reactivity patterns of 20H11 and 3C1 surprisingly show that the type b flagella has at least two separate epitopes that can be identified by monoclonal antibodies.

The extensive cross-reactivity of antibodies 21B8 and 20H11 with *P. aeruginosa* clinical isolates indicates the particular clinical utility of these antibodies in immunotherapy of *P. aeruginosa* infections.

From the foregoing, it will be appreciated that the cell lines of the present invention provide means for producing monoclonal antibodies and fragments thereof reactive with *P. aeruginosa* flagella and cross-protective against various *P. aeruginosa* strains. This allows prophylactic and therapeutic compositions to be more economically and easily produced for use against infections due to most *P. aeruginosa* strains. In addition, the cell lines provide antibodies which find uses in immunoassays and other well-known procedures.

Although the present invention has been described in some detail by way of illustration and example for purposes of clarity of understanding, it will be obvious that certain changes and modifications may be practiced within the scope of the appended claims.

We claim:

1. A composition comprising a monoclonal antibody or binding fragment thereof capable of specifically reacting with *P. aeruginosa* bacteria flagella and protective in vivo against said bacteria.

2. A composition according to claim 1, wherein said monoclonal antibody is human.

3. A composition according to claim 1, wherein said monoclonal antibody reacts with *P. aeruginosa* flagella type a or type b, but not both.

4. A composition according to claim 1, wherein said monoclonal antibody reacts with at least about 70% of type b flagella.

5. A composition comprising a monoclonal antibody capable of specifically reacting with a *P. aeruginosa* bacteria flagellar protein epitope, wherein the monoclonal antibody is capable of blocking the binding to the epitope of monoclonal antibodies produced by cell lines designated ATCC Accession Nos. HB9129, HB9130, CRL9300, and CRL9301.

6. A composition comprising one or more monoclonal antibodies, wherein a first of said monoclonal antibodies is capable of reacting with an epitope of type a flagella of *P. aeruginosa* and a second of said monoclonal antibodies is capable of reacting with an epitope of type b flagella of *P. aeruginosa*, and wherein said first and second monoclonal antibodies are protective in vivo against *P. aeruginosa*.

7. A composition according to claim 6, wherein said first antibody is a human monoclonal antibody.

8. A composition according to any of claims 1, 5, 6 or 7, further comprising a gamma globulin fraction from human blood plasma and/or an antibiotic agent.

9. A pharmaceutical composition comprising a composition according to any of claim 1, 5, 6 or 7, and a physiologically acceptable carrier.

10. A cell line which produces a monoclonal antibody capable of specifically reacting with type a or type b *P. aeruginosa* flagella, wherein the monoclonal antibody is protective in vivo against *P. aeruginosa*.

11. A cell line according to claim 10, which is a hybrid cell line.

12. A cell line according to claim 10, which produces human monoclonal antibodies.

13. A cell line which produces a monoclonal antibody capable of specifically reacting with type a or type b *P. aeruginosa* flagella, which cell line is one of ATCC Accession Nos. HB9129, HB9130, or CRL9300 and CRL9301.

14. A method of producing monoclonal antibodies specific for flagellar proteins of *P. aeruginosa* and capable of treating or preventing *P. aeruginosa* infections, said method comprising:
cultivating at least one of the cell lines of claim 13 and recovering said antibodies.

15. A method for treating a human susceptible to bacteremia and/or septicemia which comprises:
administering to said human a prophylactic or therapeutic amount of monoclonal antibodies produced according to claim 14.

16. A method of treating a human susceptible to bacterial infections, which comprises.
administering to said human a prophylactic or therapeutic amount of a monoclonal antibody capable of binding to the flagella of *P. aeruginosa* bacteria and protective in vivo against said bacteria in combination with one or more of: a prophylactic or therapeutic amount of a monoclonal antibody capable of reacting with *P. aeruginosa* exotoxin A; a monoclonal antibody capable of reacting with at least one serotype determinant on a lipopolysaccharide molecule of *P. aeruginosa*; a gamma globulin fraction from human blood plasma; a gamma globulin fraction from a human blood plasma exhibiting elevated levels of immunoglobulins reactive with *P. aeruginosa* and/or products thereof; or an antimicrobial agent.

17. A pharmaceutical composition useful for treating or preventing a *Pseudomonas aeruginosa* infection, said composition comprising a monoclonal antibody reactive with a flagellar protein of *Pseudomonas aeruginosa* and protective in vivo, an antimicrobial agent, a gamma globulin fraction from human blood plasma and a physiologically acceptable carrier.

18. A pharmaceutical composition according to claim 17, wherein the antibody is a human monoclonal antibody and the gamma globulin fraction from human blood plasma is obtained from humans exhibiting elevated levels of immunoglobulins reactive with *Pseudomonas aeruginosa* bacteria and/or products thereof.

19. A pharmaceutical composition comprising at least two monoclonal antibodies, each specifically reacting with a different type of *Pseudomonas aeruginosa* flagellar protein and capable of treating or preventing *Pseudomonas aeruginosa* infections.

20. A composition according to claim 19, wherein at least one of the monoclonal antibodies is a human monoclonal antibody.

21. A composition according to claim 19, further comprising at least one human monoclonal antibody capable of reacting with at least one serotypic determinant on a lipopolysaccharide molecule of *Pseudomonas aeruginosa* and/or a monoclonal antibody reactive with exotoxin A.

22. A method for treating a human susceptible to bacteremia and/or septicemia, which comprises:
administering to said human a prophylactic or therapeutic amount of a composition according to any of claims 17, 19, 20, 1, 2, 3, or 4.

* * * * *